(12) United States Patent
Reymond et al.

(10) Patent No.: US 8,876,733 B2
(45) Date of Patent: Nov. 4, 2014

(54) MULTIPURPOSE MALE FLUIDIC COUPLING FOR A COUPLING DEVICE AND DEVICE SUCH AS THIS INCORPORATING IT

(75) Inventors: Jean-Marc Reymond, Saint-Remy-les-Chevreuse (FR); Annabelle Hamelin, Saint-Cheron (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 962 days.

(21) Appl. No.: 13/054,341

(22) PCT Filed: Jul. 16, 2009

(86) PCT No.: PCT/FR2009/000871
§ 371 (c)(1),
(2), (4) Date: May 17, 2011

(87) PCT Pub. No.: WO2010/007254
PCT Pub. Date: Jan. 21, 2010

(65) Prior Publication Data
US 2011/0288442 A1 Nov. 24, 2011

(30) Foreign Application Priority Data
Jul. 18, 2008 (FR) .................................. 08 04125

(51) Int. Cl.
*A61B 5/00* (2006.01)
(52) U.S. Cl.
USPC ........................................................ 600/573
(58) Field of Classification Search
USPC .......... 600/573, 581; 604/181, 264, 272, 523, 604/535
See application file for complete search history.

(56) References Cited

U.S. PATENT DOCUMENTS 5,964,737 A 10/1999 Caizza
6,585,691 B1* 7/2003 Vitello .......................... 604/111
(Continued)

FOREIGN PATENT DOCUMENTS

DE 44 03 630 A1 8/1995
EP 0 978 292 A1 2/2000
(Continued)

OTHER PUBLICATIONS

International Search Report for Application No. PCT/FR2009/000871 dated Jan. 18, 2010.
International Preliminary Report on Patentability for Application No. PCT/FR2009/000871 Jul. 30, 2010.

*Primary Examiner* — Max Hindenburg
(74) *Attorney, Agent, or Firm* — Alston & Bird LLP

(57) ABSTRACT

The present invention relates to a male fluid coupling to be pushed into a female coupling in order to form a fluidic coupling device with no dead volume able to transfer a fluid, and to such a device. The female coupling (102) is coupled to a first pipe (C1) communicating with a second pipe (C2) passing through the male coupling, this female coupling having an internal push-fitting surface (103) ending in a female end (104) at which the first pipe emerges, and male coupling comprises an external push-fitting surface (106) ending in a male end (107) intended to lie inside the female coupling. This second pipe is pushed into the male coupling beyond the male end and has a free end (110) pressed fluid tightly against the female end by return means (111) which, during a push-fitting operation, collaborate with guiding and retaining means (114) designed to guide this second pipe as it slides through the male coupling while keeping this free end against the female end so as to eliminate any dead volume between the first pipe and the male coupling, making this male coupling compatible with all kinds of corresponding female couplings.

19 Claims, 1 Drawing Sheet

(56) References Cited

U.S. PATENT DOCUMENTS

| | | |
|---|---|---|
| 7,338,474 B2 * | 3/2008 | Kirk .............................. 604/240 |
| 7,815,614 B2 * | 10/2010 | Fangrow, Jr. .................. 604/256 |
| RE43,597 E * | 8/2012 | Johnson et al. .......... 604/164.04 |
| 8,551,074 B2 * | 10/2013 | Hoffman et al. .............. 604/535 |
| 8,608,710 B2 * | 12/2013 | Zhao .............................. 604/240 |

FOREIGN PATENT DOCUMENTS

| | | |
|---|---|---|
| EP | 2 005 882 A1 | 12/2008 |
| FR | 2 395 037 A1 | 1/1979 |

* cited by examiner

MULTIPURPOSE MALE FLUIDIC COUPLING FOR A COUPLING DEVICE AND DEVICE SUCH AS THIS INCORPORATING IT

FIELD OF THE INVENTION

The present invention relates to a male fluidic coupling to be press fitted into a female coupling coupled to a first conduit intended to communicate with a second conduit passing through the male coupling, in order to form a fluidic coupling device free of dead volume and able to transfer a fluid, and such a device. The invention applies more particularly, but not exclusively, to the transfer of liquid microsamples that are to be collected or to be injected.

BACKGROUND OF THE INVENTION

The fluidic coupling devices that are used in medicine and biology in association with a catheter or the like, on the one hand, and with a flexible microtube, on the other hand, are usually standardized couplings of the "Luer" type, defined by the ISO 59461 standard of 1986, or of the "Luer Lock" type, defined by the ISO 594-2 standard of 1998. Referring to FIG. 1 appended to the present description, the usual coupling devices 1 essentially comprise:
- a female coupling 2 into which a catheter is intended to be pushed and which comprises a conical internal fitting surface 3 that narrows toward a female end 4 at which the catheter emerges, and
- a male coupling 5 which is press fitted into the female coupling 2 via its conical external surface 6 with the same conicity as the internal surface 3 of the female coupling and which narrows toward a male end 7, leaving, in the state of maximal insertion, an axial distance d1 from the female end 4. By way of example, FIG. 1 shows the position of maximal insertion 7' that the male end 7 can have; it therefore leaves a free space (dead volume) of which the axial depth is d1, this being minimal when the surface 7 occupies the position 7'.

Table 1 below lists the main dimension characteristics of the coupling devices of the "Luer" type (6% conicity angle) depending on the material used, according to the aforementioned standard.

TABLE 1

| Dimensional parameter | | Description | Dimensions (mm) Rigid material | Dimensions (mm) Semirigid material |
|---|---|---|---|---|
| Base dimensions | $d_{min}$ | Minimum diameter of the end of the male conical coupling (reference diameter) | 3.925 | 3.925 |
| | $d_{max}$ | Maximum diameter of the end of the male conical coupling | 3.990 | 4.027 |
| | $D_{min}$ | Minimum diameter of the opening of the female conical coupling | 4.270 | 4.270 |
| | $D_{max}$ | Maximum diameter of the opening of the female conical coupling | 4.315 | 4.315 |
| | E | Minimum length of the male conical coupling | 7.500 | 7.500 |
| | F | Minimum depth of the female conical coupling | 7.500 | 7.500 |
| Other dimensions | L* | Minimum penetration | 4.665 | 4.050 |
| | M* | Variance over the penetration of the female coupling | 0.750 | 0.750 |
| | N* | Variance over the penetration of the male coupling | 1.083 | 1.700 |
| | $R^{**}_{max}$ | Radius of curvature | 0.5 | 0.5 |

With reference to the symbols * and ** of this table:
*the dimensions L, M, N result from the base dimensions, and
**or equivalent entry chamfer not having sharp angles.

A major drawback of the coupling devices defined by the aforementioned standards is that the distance d1 (typically of about 3 to 6 mm depending on the type of female coupling used) between the respective ends of the male and female couplings generates a cavity forming an intrinsic dead volume that becomes disadvantageous in various circumstances. The most frequent is when the couplings are used for circulating very small samples of liquid, of an order of magnitude comparable to or even smaller than this dead volume. By way of example, when injecting or collecting microsamples of mammalian blood, it is general practice to use a flexible conduit provided with a coupling having a diameter of about 4 mm, the space thus delimited determining a dead volume of the order of 35 µl (for a cavity with a length of 3 mm) to 70 µl (for a cavity with a length of 6 mm), which dead volume may cause the following problems in use, on account of these relatively large dimensions:
- since several successive microsamples serve to fill this dead volume, this delays the passage of the first microsamples and means that a larger volume of fluid is collected, which is lost, and
- since the cross section of the fluidic conduit is considerably widened on account of this dead volume, various microsamples become mixed up there with one another, which is disadvantageous if the fluid is a liquid, and if these microsamples are used subsequently, for example for the purpose of analysis. This impairs their traceability and is particularly disadvantageous when monitoring processes that develop over the course of time, for example rapid biological phenomena, during which it is of fundamental importance for each microsample to be able to retain its initial characteristics throughout the process.

Moreover, and as is shown in Table 1 above, the standards relating to the "Luer" couplings do not define a single type of coupling, especially as regards female couplings, but several types that are mutually compatible and that have dimensions in part defined in this table (these standards do not specify, for example, the dimension of the cavity between the male and female couplings). As a result, any coupling device of the "Luer" or "Luer Lock" type minimizing this dead volume must aim for compatibility with all the various dimensions of these different types, so as not to make it too difficult for users to manage the procurement of couplings.

It is also known from document U.S. Pat. No. 4,966,588 to use, for the injection of a therapeutic liquid substance, a fluidic coupling device essentially comprising:

a male coupling press fitted into a female coupling via respective cylindrical fitting surfaces provided with shoulders, this female coupling being intended to receive a cannula forming an injection tip, and a rigid injection needle which is inserted so as to pass through the male coupling and the female coupling and also the cannula, by piercing a sealing washer positioned between the two couplings, and which is intended to be implanted in the body to be treated.

This coupling device with a rigid injection needle passing right through the couplings and the cannula does indeed make it possible to minimize the dead volume, but it has the following drawbacks:

the diameter of the needle is small by comparison with that of the opening of the male coupling and of the fluidic conduit, which significantly reduces the flow rate and is reflected in an increased speed of the fluid (the viscosity of the latter can then pose a problem);

this device may be effective only for a single coupling procedure, since there is nothing to suggest that subsequent couplings would have the needle pass through the same orifice of the sealing washer (there being a possibility of the latter being unintentionally displaced following removal of the needle after each injection) or that this washer would then have the same leaktightness;

this device does not comply with the aforementioned "Luer" or "Luer Lock" types; and the needle necessarily extends beyond the sealing washer by a length that may cause problems in certain applications upstream or downstream of this needle (for example when the cannula is formed by a flexible catheter, the needle may extend beyond the end of the catheter, causing it to lose its flexibility and thereby risking possible damage to the surrounding biological tissue).

Current developments in biomedical techniques mean that it is increasingly common to use liquid microsamples (i.e. samples each having a volume of less than 100 μl and preferably less than or equal to 30 μl, such as blood samples collected from small animals). However, the sampling lines that comprise at least one coupling device of the "Luer" or "Luer Lock" type must be able to maintain the traceability of these microsamples, allowing the microsamples to be retrieved at the output end as they were at the input end. These couplings must additionally have a leaktightness that is not significantly affected by the clamping force between the male and female couplings or damaged by a succession of several assembling and dismantling procedures.

Document DE-A1-44 03 630 discloses a complex assembly of several tubes and male and female couplings in which it is the female coupling (see FIG. 3) that is modified in order to minimize the dead volume, it being noted specifically that the male coupling is in this case screwed and not just press fitted into this female coupling.

Document U.S. Pat. No. 5,964,737 discloses, in FIG. 19 thereof, a syringe terminating in a male connector piece which is press fitted into a female connector piece but which in particular does not have any flexible tube or conduit passing through it.

SUMMARY OF THE INVENTION

It is an object of the present invention to make available a male fluidic coupling intended to be press fitted into a female fluidic coupling coupled to a first conduit intended to communicate with a second conduit passing through the male coupling, in order to form a fluidic coupling device able to transfer a fluid, which device overcomes all the aforementioned drawbacks and which also allows a single male coupling to adapt equally to all the types of female couplings defined by the aforementioned standards of the "Luer" and "Luer Lock" couplings, this female coupling comprising a radially internal press fitting surface terminating in a female radial end at which this first conduit emerges, the male coupling comprising a radial press fitting surface terminating in a first male radial end intended to be located inside the female coupling.

For this purpose, a device according to the invention is such that this second conduit is formed by a flexible tube which is pushed into the male coupling axially beyond said first male end and terminates in a free end that is able to be pressed in a leaktight manner against said female end by return means which are integrated in the male coupling, these return means cooperating, during the press fitting, with guiding and retaining means provided in the male coupling in order to guide this tube in an axial sliding movement through the male coupling by bringing said free end close to said first male end while keeping this free end against said female end, so as to eliminate any dead volume between the first conduit and the male coupling.

It will be noted that these return means exert, over the entire useful travel of the tube, a force sufficient to ensure leaktightness.

It will also be noted that the coupling devices incorporating this male coupling according to the invention are such that the fluid to be transferred can equally flow through them in one or other direction (i.e. for injection or sampling).

It will additionally be noted that if the fluid transferred is a liquid, the coupling devices incorporating this male coupling according to the invention overcome the aforementioned drawbacks associated with the dead volume generated between the male and female couplings, thereby avoiding in particular the mixing together of microsamples.

According to another feature of the invention, said return means may be able to be axially compressed during the sliding of the tube toward the inside of the male coupling, in such a way that said free end is pressed against said female end with a force resulting at least in part from the compression of the return means due to the clearance of said tube during its sliding, this clearance being greater than the axial depth of the female coupling as measured from said female end.

To ensure that the leaktightness is effective from the start of the travel of the tube inside the male coupling, and that the clearance does not significantly exceed the useful travel for the various types of female couplings, these return means can advantageously be prestressed. In other words, said pressing force then results not only from the compression of said return means during the clearance of the tube but also from a prestressing applied to these return means before the male coupling is mounted in the female coupling, the prestressing being such that, once the tube starts sliding, said free end of the tube is substantially able to ensure the leaktightness with respect to the female coupling (i.e. is placed under conditions close to those ensuring leaktightness), and a slight compression of the return means during the sliding makes it possible to confer on the pressing force an intensity sufficient to ensure leaktightness.

It will be noted that the prestressing allows this force to vary minimally over the entire useful travel of the tube inside the male coupling. However, the less the variation of this force, the better the compatibility of the male coupling according to the invention with all the types of female couplings mentioned in particular in the aforementioned standards.

With or without this prestressing, the functional specifications of these standards are met and the leaktightness is made quasi-independent of the clamping force between the two couplings and of the wear resulting from several fittings/dismantlings, on account of the fact that the free end of the tube abuts on the internal radial end of the female coupling with a pressure sufficient to guarantee the leaktightness of this abutment by virtue of said return means. This pressure results from the force created by the compression of the return means, resulting from the clearance of the tube, which slides inside the coupling, and, if appropriate, from said initial prestressing.

As has been indicated above, it will be noted that this multipurpose aspect of a male coupling according to the invention with various female couplings of different axial depths is made possible by the fact that the tube, before fitting, protrudes by a sufficient length in relation to said first male end, this protrusion generating, during the fitting, the return of this tube in the opposite direction, which is reflected by the thrust provided by the return means pressing the tube against said female end.

According to another feature of the invention, said return means can be mounted abutting, on the one hand, against a radial end wall of the male coupling opposite said first male end and, on the other hand, against at least one radial bearing surface which is integral with said tube. Said return means can advantageously comprise a helical compression spring mounted radially between said tube and this male coupling.

According to another advantageous feature of the invention, said guiding and retaining means can be designed to stiffen said tube along a stiffened portion of the latter extending axially inside the male coupling and terminating beyond said first male end at a distance from said free end, in such a way that this tube has a flexible end portion with a stiffness less than that of this stiffened portion and able to ensure the leaktightness of the connection between said free end and said female end by supporting the return force generated by said return means against said female end.

It will be noted that this stiffened portion, which corresponds to that part of the tube stressed by the return means, makes it possible to prevent buckling of the tube inside the male coupling, in association with this flexible end portion, which has dimensions intended to prevent buckling of the tube in the apical zone of elastic deformation of the latter ensuring the leaktightness of said free end with said female end.

According to a preferred embodiment of the invention, said guiding and retaining means comprise a rigid tubular sleeve mounted integrally on said tube by tightly enclosing it along said stiffened portion, for example a metal or plastic sleeve, the flexible end portion of said tube being without this sleeve, which is mounted so as to slide axially inside the male coupling by passing through said first male end and a second, opposite male end of the male coupling. Said radial bearing surface for said return means is in this case formed by a circumferential flange of said sleeve.

According to an alternative embodiment of the invention, said stiffened portion can be an integral part of said tube, having a stiffness greater than that of said flexible end portion of this tube, this stiffened portion being obtained by treatment involving local hardening of the tube.

According to another feature of the invention common to said preferred embodiment and to this alternative embodiment, said guiding and retaining means can additionally permit a free rotation of said tube inside the male coupling.

Preferably, said external press fitting surface of the male coupling is a conical surface that narrows toward said first male end with a conicity identical to that of said internal press fitting surface of the female coupling.

More preferably still, the male coupling is of the "Luer" type, as defined by the ISO 59461 standard of 1986, or of the "Luer Lock" type, as defined by the ISO 594-2 standard of 1998.

A fluidic coupling device according to the invention, which is able to transfer a fluid, for example microsamples to be collected or injected, and which is intended to be connected to a first conduit via a first opening of this device, which has a second opening traversed by a second conduit intended to communicate with the first conduit in order to transfer this fluid, comprises:

a female fluidic coupling, which defines the first opening and which comprises a radially internal press fitting surface terminating in a female radial end at which this first conduit emerges, and a male fluidic coupling, which defines the second opening by being press fitted into the female coupling via a radially external press fitting surface and which terminates in a male radial end inside the female coupling.

According to the invention, this male coupling is as defined above.

Preferably, the male coupling and female coupling are both of the "Luer" type, as defined by the ISO 59461 standard of 1986, or both of the "Luer Lock" type, as defined by the ISO 594-2 standard of 1998.

More preferably still, the male coupling and female coupling are both of the "Luer Lock" type, as defined by the ISO 594-2 standard of 1998, the male coupling then being able to have a circumferential lug bent radially inward and surrounding said external press fitting surface, and an end shoulder protruding radially outward on the female coupling locks itself between this lug and this external press fitting surface in order to avoid the male coupling and female coupling moving away from each other.

According to another feature of the invention, before press fitting, said tube advantageously extends beyond said first male end by an initial axial distance that is greater than the maximum axial depth of the female couplings according to one or other of said standards, as measured from said radial female end. As has been indicated above, this tube is able to slide inside the male coupling during press fitting with an axial clearance at the end of the sliding that is equal to or greater than 8 mm, in such a way that this tube is returned with a sufficient pressure against said female end regardless of the axial depth of the female coupling chosen.

It will be noted that, in contrast to the standard coupling devices of the "Luer" or "Luer Lock" type, in which the leaktightness is achieved by the fit of the respective conical fitting surfaces of the male and female couplings, the device of the invention is designed to provide the leaktightness close to the inlets/outlets and directly via said free end of the tube.

Said first conduit passing through the female coupling is advantageously a flexible microtube suitable for collecting said liquid from an animal or for injecting said liquid into an animal, such as a flexible catheter to be implanted in the caudal vein of a small mammal for the purpose of collecting microsamples of blood.

BRIEF DESCRIPTION OF THE DRAWINGS

The aforementioned features of the present invention, together with others, will be more clearly understood on reading the following description of several embodiments of the invention, given by way of nonlimiting illustration, said description referring to the appended drawing in which.

DETAILED DESCRIPTION OF THE INVENTION

Figure 1:
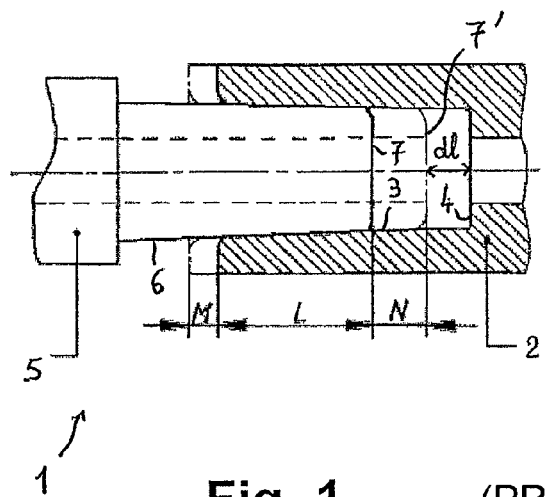
FIG. 1 is a partial view, in radial section, of a known coupling device which has male and female couplings of the "Luer" type and which is intended to be connected, on the one hand, to a catheter and, on the other hand, to a flexible microtube for collecting microsamples.
Figure 2:
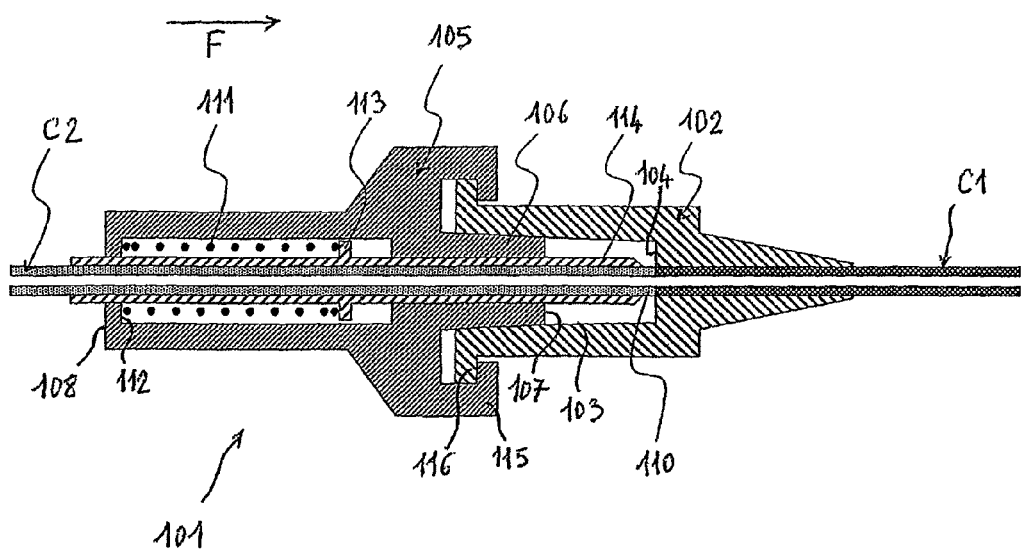
FIG. 2 is a schematic view, in radial section, of a coupling device with male and female couplings according to the invention of the "Luer Lock" type, which are connected to each other in a leaktight manner by being traversed by microtubes for the transfer of a fluid.

As is illustrated in FIG. 2, the coupling device 101 according to the invention is in this example of the "Luer Lock" type (with reference to the ISO 594-2 standard of 1998), and it essentially comprises:

- a female fluidic coupling 102 into which a first conduit C1, such as a flexible catheter, is pushed, and which has a radially internal conical press fitting surface 103 narrowing toward a female radial end 104 at which the first conduit C1 emerges (this end 104 can be flat or slightly conical), and
- a male fluidic coupling 105 which is press fitted into the female coupling 102 via its radially external conical press fitting surface 106 with the same conicity as the internal surface 103, and which narrows toward a male radial end 107, a second flexible conduit C2, such as a microtube, being pushed into the male coupling 105 and passing through the two ends 107 and 108 of the latter and coming into abutment in a leaktight manner against the female end 104.

According to an important feature of the invention, the free end 110 of the flexible conduit C2 is able to be pressed in a leaktight manner against the female end 104 by a helical compression spring 111 made of metal and mounted radially between the conduit C2 and the male coupling 105 and abutting axially against a radial internal end wall 112 of the male coupling 105 opposite the male end 107 and against a radial bearing surface 113 which is integral in translation with the conduit C2, via guiding and retaining means 114 with which the conduit C2 is provided in order to guide it in an axial sliding movement through the male coupling 105 and in order to keep the free end 110 thereof in leaktight abutment against the female end 104.

In the embodiment illustrated in FIG. 2, these guiding and retaining means 114 are formed by a rigid tubular sleeve (such as a metal sleeve, or a sleeve made of plastic, for example a polymeric resin), which is mounted integrally on the flexible conduit C2, along the greater part of the length thereof, so as to slide axially therewith through the male coupling 105, thus stiffening it along the entire portion where it is enclosed by this sleeve 114 (this stiffened portion passes axially through the male coupling 105 and protrudes from the ends 107 and 108 thereof but it terminates at a distance from the free end 110 of the conduit C2), and which has the bearing surface 113 in the form of a circumferential flange for the spring 111. This flange 113 can be obtained by expansion rolling in the case of a metal sleeve 114, or by molding or by extrusion in the case of a plastic sleeve 114.

This axial offset between the sleeve 114 and the free end 110 of the conduit C2 means that the latter has a flexible end portion able to ensure the leaktightness of the connection under pressure between the conduit C2 and the female end 104, by supporting the return force F generated by the spring 111. This flexible end portion of the conduit C2 can, for example, have an axial length of about 1 mm, in such a way as to ensure this leaktightness by elastic deformation.

As will be explained below, this sliding fit of the sleeve 114 enclosing the conduit C2 is designed to ensure that the free end 110 of the latter comes close to the male end 107 while being returned with a sufficient pressure against the female end 104 by the axial compression of the spring 111, thereby eliminating any dead volume between the first conduit C1 and the male coupling 105.

As is illustrated in FIG. 2, the external diameter of the sleeve 114 is chosen to be less than the smallest internal diameter of the female coupling 102, regardless of whether the latter is of the "Luer" or "Luer Lock" type. This sleeve 114 intended to prevent buckling of the conduit C2 is formed from a material whose stiffness is at least as great as that of the material of this conduit C2. It is preferably formed by a thin metal tube, or by a tube made of a material having sufficient stiffness, for example a polymeric resin or another plastic material. This is because the conicity of the "Luer" or "Luer Lock" devices necessitates a small diameter of the sleeve 114, particularly near the leaktight joint between the conduit C2 and the female end 104, where the diameter of the coupling cone 102 is smallest. This results in the choice of a sleeve 114 of small thickness and therefore of high stiffness. In the leaktight connection position, it is important that the sleeve 114 is not the site of a bending or buckling under the pressure of maintaining the free end 110 of the flexible conduit C2 against the female end 104. It will be noted that the section of this free end 110 must necessarily have a symmetry of revolution, defined preferably by a flat surface perpendicular to the axis of symmetry of the conduit C2. However, according to other embodiments, the section of this free end 110 could have a truncated surface or, alternatively, one or more chamfers, provided that the latter meet(s) this condition of symmetry of revolution.

The male coupling 105 in FIG. 2 has been obtained from a standard "Luer Lock" male coupling, with a central axial bore having been formed in this coupling 105 along the entire length thereof in order to introduce into it the movable assembly composed of the flexible conduit C2 and of the stiffening sleeve 114.

According to an alternative not illustrated in FIG. 2, these guiding and retaining means for the conduit C2 could be obtained by a specific treatment involving local hardening of this conduit C2 in proximity to the free end 110 thereof, while allowing the latter a sufficient flexibility to ensure the leaktightness by abutment against the female end 104.

More precisely, the spring 111 is such that its pre-compression ensures sufficient leaktightness via this abutment, even for the female couplings 102 used with the greatest depth in the axial direction (i.e. for the shortest travel of the spring 111). As regards the initial length, before press fitting, by which the conduit C2 extends beyond the male end 107, it is chosen to be sufficient to ensure this leaktightness with the female end 104, the abutment pressure at the leaktight joint depending on the thrust of the spring 111.

It will be noted that the device 101 of the "Luer Lock" type illustrated in FIG. 2 is such that the male coupling 105 has a circumferential lug 115 bent radially inward and surrounding the external press fitting surface 106 of the coupling 105, and that the female coupling 102 has an end shoulder 116 protruding radially outward and locking itself between this lug 115 and this external press fitting surface 106. This locking avoids the two couplings 102 and 105 moving away from each other.

It will be noted, however, that a coupling device according to the invention could also entail couplings of the "Luer" type without a locking element, but that in this case there is a risk of accidental disconnection if the couplings have not been coupled sufficiently strongly to each other, i.e. if the return force resulting from the pressure of the spring 111 and from the pressure of the fluid becomes greater than the press fitting force of the male and female conical couplings.

A coupling device 101 according to the invention, such as the one illustrated in FIG. 2, is brought into the position of leaktight connection in the following way.

Before the male coupling 105 is press fitted, the conduit C2 provided with its guiding and retaining means (such as the sleeve 114 in the example in FIG. 2) extends beyond the male end 107 by a length that is greater than the maximum internal depth of all the usable female couplings 102.

When the male coupling 105 is push-fitted into the female coupling 102 chosen, the flexible free end 110 of the conduit C2 is kept in leaktight contact with the female end 104 via the spring 111, which ensures a sufficient thrust (arrow F) to press this end 110 there in a leaktight manner.

For this purpose, when assembling the device 101, the spring 111 receives a prestressing so as to ensure this sufficient thrust even on the deepest female couplings 102, this thrust being calculated in such a way as to guarantee a minimum pressure hold of the joint of 330 kPa according to the ISO 594-2 "Luer Lock" standard of 1998, and regardless of which female coupling 102 is chosen. Thus, for a relatively deep female coupling 102, this pressure will be 400 kPa for example, whereas the same male coupling 105 mounted on a "Luer Lock" female coupling 102 of less depth will have its spring 111 more strongly compressed, increasing by proportion the maximum pressure admissible for the joint at the abutment, for example 600 kPa (in order to calculate the holding pressure of the joint, the return force exerted by the spring 111, which is a function of the compression thereof, is divided by the surface area of the joint as defined by the surface area of the section of the flexible conduit C2 at the free end 110 thereof).

It will be appreciated that, by using a spring 111 of great length, the pressure difference on this joint is reduced for a connection on a "Luer" or "Luer Lock" female coupling of less depth, by comparison with a female coupling of the same type but deeper.

As regards the clearance of the sleeve 114 following its sliding movement inside the male coupling 105, this clearance is greater than the maximum difference of internal depth—of about 6 mm—between the different types of female couplings of the "Luer" or "Luer Lock" range, and this clearance is consequently greater than 8 mm.

The preferred application of a coupling device according to the invention concerns a catheterization line for microsamples of liquid fluid. By virtue of this device, any catheterization line using standard "Luer" or "Luer Lock" female couplings allows these microsamples to be transferred without risk of their mixing, and this permits perfect traceability (the microsamples at the output of the line matching those at the input of the line). In addition, there is no need to wait for a large number of microsamples to be collected before starting the measurements or analyses, and this avoids wasting a volume of liquid corresponding to the dead volume of the prior art. By way of example, for coupling to a catheter C1 with an internal diameter of 1 mm, a flexible tube C2 with an internal diameter equal to 1 mm will preferably be used.

However, it will be noted that a coupling device according to the invention could also be used in certain applications using high-volume samples or not requiring traceability in time and space, the advantage of this other use being the reduction in the number of soiled parts and in the residual quantity of fluid after manipulation, in the case of the treatment of liquids that require particular monitoring (e.g. contaminated blood, radioactive liquids, etc.).

The invention claimed is:

1. A male fluidic coupling configured to be press fitted into a female fluidic coupling connected to a first conduit intended to communicate with a second conduit passing through the male coupling, in order to form a fluidic coupling device able to transfer a fluid, such as microsamples that are to be collected or to be injected, the female coupling comprising an internal press fitting surface terminating in a female radial end at which said first conduit emerges, the male coupling comprising an external press fitting surface terminating in a first male radial end intended to be located inside the female coupling, wherein said second conduit is formed by a flexible tube which is pushed into the male coupling axially beyond said first male end and which terminates in a free end, said free end having a symmetry of revolution and being able to be pressed in a leaktight manner against said female end by return means which are integrated in the male coupling, said return means cooperating, during the press fitting, with guiding and retaining means provided in the male coupling in order to guide said tube in an axial sliding movement through the male coupling by bringing said free end close to said first male end while keeping said free end against said female end, so as to eliminate any dead volume between the first conduit and the male coupling.

2. The male fluidic coupling as claimed in claim 1, characterized in that said return means are able to be axially compressed during the sliding of said tube toward the inside of the male coupling, in such a way that said free end is pressed against said female end with a force resulting at least in part from the compression of the return means due to the clearance of said tube during its sliding, said clearance being greater than the axial depth of the female coupling as measured from said female end.

3. The male fluidic coupling as claimed in claim 2, characterized in that said pressing force results not only from the compression of said return means during the clearance of said tube but also from a prestressing applied to said return means before the male coupling is mounted in the female coupling, this prestressing being such that, once the tube starts sliding, said free end of said tube is substantially able to ensure the leaktightness with respect to the female coupling, and a slight compression of said return means during said sliding makes it possible to confer on said pressing force an intensity sufficient to ensure leaktightness.

4. The male fluidic coupling as claimed in claim 2, characterized in that said return means are mounted abutting, on the one hand, against a radial end wall of the male coupling opposite said first male end and, on the other hand, against at least one radial bearing surface which is integral with said tube.

5. The male fluidic coupling as claimed in claim 4, characterized in that said return means comprise a helical compression spring mounted radially between said tube and said male coupling.

6. The male fluidic coupling as claimed in claim 1, characterized in that said guiding and retaining means are designed to stiffen said tube along a stiffened portion of the latter extending axially inside the male coupling and ending beyond said first male end at a distance from said free end, in such a way that said tube has a flexible end portion with a stiffness less than that of said stiffened portion and able to ensure the leaktightness of the connection between said free end and said female end by supporting the return force generated by said return means against said female end, said respectively stiffened and flexible portions being designed to prevent buckling of said tube inside the male coupling and against said free end.

7. The male fluidic coupling as claimed in claim 6, characterized in that said guiding and retaining means comprise a rigid tubular sleeve mounted integrally on said tube by tightly enclosing it along said stiffened portion, said flexible end portion of said tube being without this sleeve, which is mounted so as to slide axially inside the male coupling by passing through said first male end and a second, opposite male end of the male coupling.

8. The male fluidic coupling as claimed in claimed in claim 7, wherein said return means are able to be axially compressed during the sliding of said tube toward the inside of the male coupling, in such a way that said free end is pressed against said female end with a force resulting at least in part from the compression of the return means due to the clearance of said tube during its sliding, said clearance being greater than the axial depth of the female coupling as measured from said female end, and wherein said return means are mounted abutting, on the one hand, against a radial end wall of the male coupling opposite said first male end and, on the other hand, against at least one radial bearing surface which is integral with said tube and being characterized in that said radial bearing surface for said return means is formed by a circumferential flange of said sleeve.

9. The male fluidic coupling as claimed in claim 6, characterized in that said stiffened portion is an integral part of said tube, having a stiffness greater than that of said flexible end portion of said tube, said stiffened portion being obtained by treatment involving local hardening of said tube.

10. The male fluidic coupling as claimed in claim 1, characterized in that said guiding and retaining means additionally permit a free rotation of said tube inside the male coupling.

11. The male fluidic coupling as claimed in claim 1, characterized in that said external press fitting surface of the male coupling is a conical surface that narrows toward said first male end with a conicity identical to that of said internal press fitting surface of the female coupling.

12. The male fluidic coupling as claimed in claim 11, characterized in that it is of the "Luer" type, as defined by the ISO 59461 standard of 1986, or of the "Luer Lock" type, as defined by the ISO 594-2 standard of 1998.

13. A fluidic coupling device which is able to transfer a fluid, for example microsamples to be collected or injected, and which is intended to be coupled to a first conduit via a first opening of said device, which has a second opening traversed by a second conduit intended to communicate with the first conduit in order to transfer said fluid, the device comprising:
    a female fluidic coupling, which defines said first opening and which comprises an internal press fitting surface terminating in a female radial end at which said first conduit emerges, and
    a male fluidic coupling, which defines said second opening by being press fitted in the female coupling via an external press fitting surface and which terminates in a first male radial end inside the female coupling,
    wherein said second conduit is formed by a flexible tube which is pushed into the male coupling axially beyond said first male end and which terminates in a free end, said free end having a symmetry of revolution and being able to be pressed in a leaktight manner against said female end by return means which are integrated in the male coupling, said return means cooperating, during the press fitting, with guiding and retaining means provided in the male coupling in order to guide said tube in an axial sliding movement through the male coupling by bringing said free end close to said first male end while keeping said free end against said female end, so as to eliminate any dead volume between the first conduit and the male coupling.

14. The fluidic coupling device as claimed in claim 13, characterized in that the male coupling and female coupling are both of the "Luer" type as defined by the ISO 59461 standard of 1986, or both of the "Luer Lock" type, as defined by the ISO 594-2 standard of 1998.

15. The fluidic coupling device as claimed in claim 14, characterized in that the male coupling and female coupling are both of the "Luer Lock" type, as defined by the ISO 594-2 standard of 1998, the male coupling having a circumferential lug bent radially inwards and surrounding said external press fitting surface, and an end shoulder protruding radially outward on the female coupling locks itself between said lug and said external press fitting surface.

16. The fluidic coupling device as claimed in claim 14, characterized in that, before press fitting, said tube extends beyond said first male end by an initial axial distance that is greater than the maximal axial depth of the female couplings according to one or other of said standards.

17. The fluidic coupling device as claimed in claim 16, characterized in that said tube is able to slide inside the male coupling, during press fitting, with an axial clearance at the end of the sliding that is equal to or greater than 8 mm, in such a way that said tube is returned with sufficient pressure against said female end regardless of the axial depth of the female coupling chosen.

18. The fluidic coupling device as claimed in claim 13, characterized in that said first conduit is a flexible microtube suitable for collecting said liquid from an animal or for injecting said liquid into an animal.

19. The fluidic coupling device as claimed in claim 18, wherein said flexible microtube comprises a flexible catheter that is configured to be implanted in the caudal vein of a small mammal for collecting microsamples of blood.

* * * * *